US006428527B1

(12) United States Patent
Jones et al.

(10) Patent No.: US 6,428,527 B1
(45) **Date of Patent: *Aug. 6, 2002**

(54) METHOD FOR COATING A BLOOD COLLECTION DEVICE

(75) Inventors: Huw David Jones, Plymouth (GB); Kent Patras, Sargent, NE (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/189,643

(22) Filed: Nov. 10, 1998

(51) Int. Cl.[7] .......................... A61B 19/00
(52) U.S. Cl. .......................... 604/403; 427/532
(58) Field of Search .......................... 604/403, 415; 600/476; 428/36.7, 36.91, 446, 448, 500, 702, 413, 480; 220/456, 457; 206/524.2; 427/532

(56) References Cited

U.S. PATENT DOCUMENTS 5,326,535 A * 7/1994 Vogler et al. ............... 422/102
5,510,155 A * 4/1996 Williams et al. ............ 427/532
5,518,615 A * 5/1996 Vogler et al. ............... 210/511
5,686,157 A * 11/1997 Harvey et al. ............. 428/36.7
5,732,885 A 3/1998 Huffman
5,738,920 A * 4/1998 Knors ........................ 428/35.9
5,763,033 A * 6/1998 Tropsha et al. ............ 428/36.7
5,906,744 A * 5/1999 Carroll et al. .............. 210/516
5,968,620 A * 10/1999 Harvey et al. ............. 428/35.9
6,013,337 A * 1/2000 Knors ........................ 427/579

FOREIGN PATENT DOCUMENTS

EP 0 766 973 A1 9/1997

* cited by examiner

*Primary Examiner*—Dennis Ruhl
(74) *Attorney, Agent, or Firm*—Richard E. Brown

(57) ABSTRACT

A blood collection assembly includes a tube having an open end with a puncturable stopper therein. A thixotropic gel for separating blood components is in the tube and a layer of additive particles is spray dried from an air nozzle onto the inside tube wall. The invention includes a method to make the tube.

5 Claims, 1 Drawing Sheet

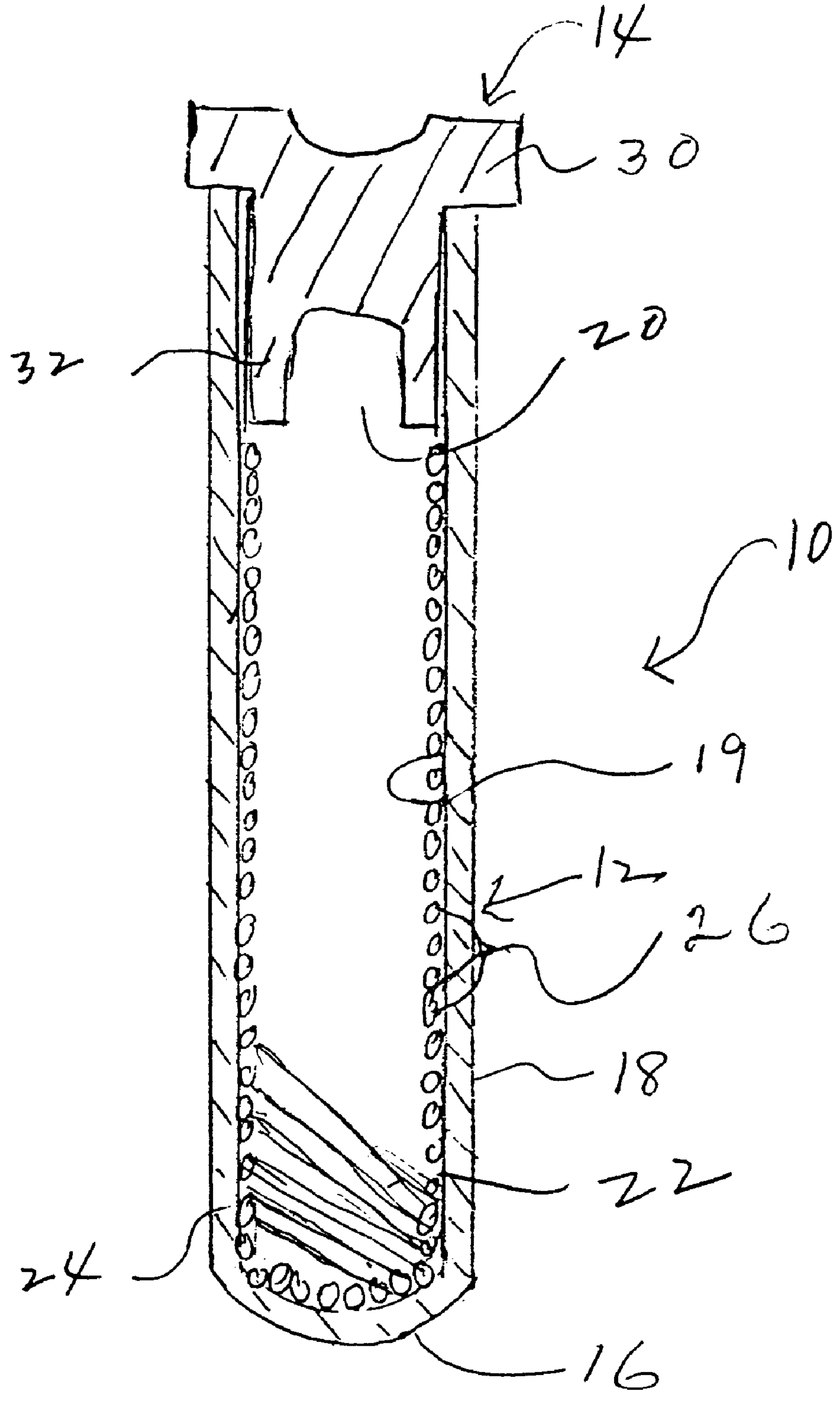
Figure

METHOD FOR COATING A BLOOD COLLECTION DEVICE

BACKGROUND OF THE INVENTION

1. Field of the Invention

This invention relates to sample collection and more particularly relates to a method for coating a blood sample collection tube.

2. Background

Blood samples are routinely taken in evacuated tubes. One end of a double-ended needle is inserted into a patient's vein. The other end of the needle then punctures a septum covering the open end of the tube so that the vacuum in the tube draws the blood sample through the needle into the tube. Using this technique, a plurality of samples can be taken using a single needle puncture of the skin.

Blood drawn into a tube is typically mixed with an additive present in the tube prior to draw. Clot activators such as silica particles promote rapid coagulation so that the liquid serum fraction can be readily separated from the clotted cells. Anticoagulants are used to prevent clotting when the blood sample is to be used directly in hematological tests or for separation of blood cells from the plasma. For separation, the blood sample is centrifuged, and a gel having a specific gravity between that of the solid and liquid fractions is used as a barrier between the fractions.

Collection tubes are conventionally made of glass or plastic, such as polyethylene terephthalate (PET). Glass tubes have the advantage of water and gas impermeability. Plastic tubes are advantageous over glass in lower breakage, less weight in shipment and easier disposal by incineration, but high permeability to water and gas is a disadvantage.

In glass it has been conventional to provide the additive in aqueous solution to provide rapid mixing with the blood. However, the action of a liquid additive in the tube may be masked by the gel. Also, if the additive is applied to the wall of the glass tube, it rapidly runs down the tube wall and collects in the bottom of the tube where, again, its action may be masked by the gel. For this reason the tube wall is often coated with polyvinylpyrrolidone (PVP) and the anticoagulant solution applied thereover. The PVP dissolves in the blood and becomes part of the plasma.

Aqueous additive formulations are unsatisfactory in plastic because moisture permeation through the tube wall changes additive concentration, may reduce additive functionality and may reduce shelf life. In one approach to providing additives in plastic tubes, a plastic blood collection tube contains a plastic film insert having an anticoagulant affixed thereto. Such tubes have the disadvantage that the film becomes part of the packed cells and can interfere with analyses which use the cells, such as blood typing.

In another approach, the inside wall of a plastic tube is spray coated with an ultrasonic coating device and the coating is air dried.

There is a need for a plastic blood collection tube having a uniform sprayed-on additive which is readily air dried to a solid form which will readily dissolve when blood enters the tube and yet leave both the plasma and cell fractions free of extraneous materials. The present invention fulfills this need.

SUMMARY OF THE INVENTION

A blood collection assembly includes a collection tube having a bottom wall continuous with a side wall. The side wall defines an open end and the bottom wall defines a closed end. Together the bottom and side walls define an inside wall surface. Preferably, the open end is covered by a puncturable stopper and the tube is evacuated. A conventional thixotropic gel may be stored in the bottom of the tube. The inside wall surface is coated with an additive for blood analysis applied by spraying a solvent dispersion of the additive through an air nozzle and drying to leave a layer of discrete particles. In this application, the term dispersion includes both a solution and a suspension.

A second aspect of the invention is a method to make the tube.

Use of an air nozzle instead of a conventional ultrasonic nozzle provides several advantages. The mist provided by an air nozzle is finer and more uniform, thereby eliminating coalescing of the spray into droplets and subsequent rundown of fluid, even on the inside wall of a glass tube. Avoiding rundown facilitates drying and gives uniform coatings of discrete solid particles of greater surface area. In addition air nozzles are much less complex than ultrasonic nozzles and therefore provide substantial cost savings and ease of adaptation for automated manufacturing lines.

BRIEF DESCRIPTION OF THE DRAWING

The FIGURE is a vertical sectional view of the tube of the invention showing the particulate nature of the additive.

DETAILED DESCRIPTION

Figure 1:
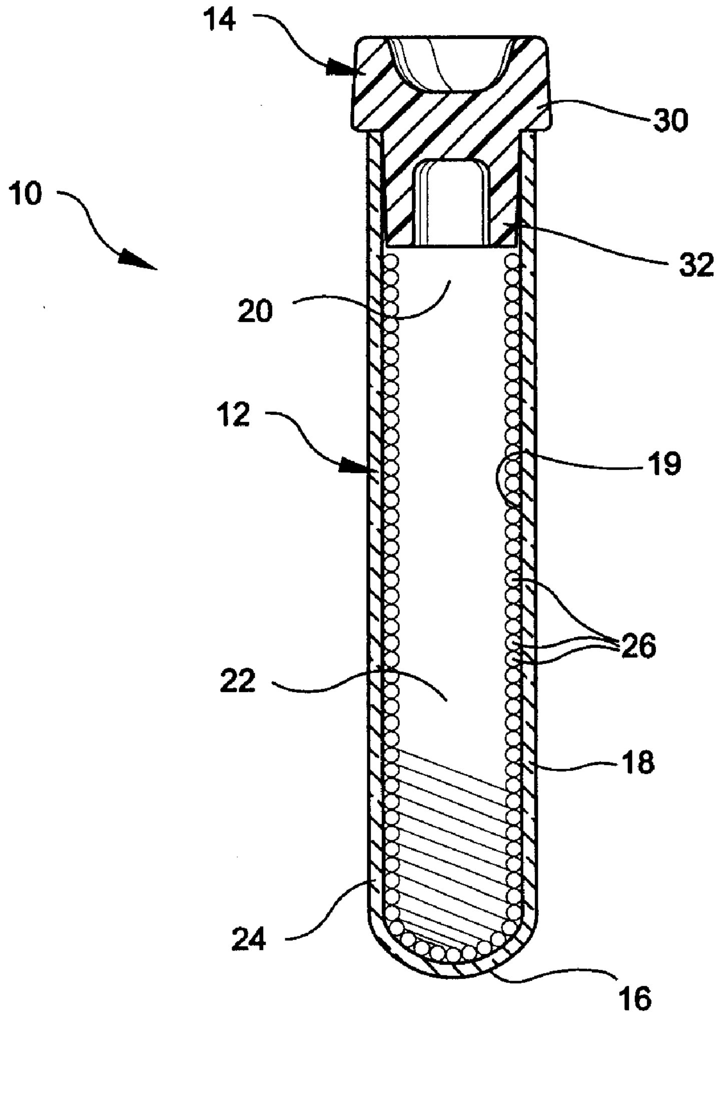

While this invention is satisfied by embodiments in many different forms, there will herein be described in detail preferred embodiments of the invention with the understanding that the present disclosure is to be considered as exemplary of the principles of the invention and is not intended to limit the invention to the embodiments illustrated and described. The scope of the invention will be measured by the appended claims and their equivalents.

The blood collection assembly of the invention may include any container, preferably plastic, having a closed end and an open end. Suitable containers are, for example bottles, vials, flasks and the like, preferably tubes. The invention will henceforth be described in terms of the preferred tube.

Adverting now to the drawing, the FIGURE illustrates a blood collection assembly 10 which includes a tube 12 and a puncturable stopper 14. Tube 12 has a bottom wall 16 and a side wall 18 having an inside wall surface 19. Side wall 18 defines an open end 20 into which the stopper 14 may be placed. Bottom wall 16, side wall 18 and stopper 14 enclose an interior volume 22 of the tube which preferably is evacuated. Tube 12 has a layer 26 of additive particles on inside wall surface 19 applied by spraying a solvent dispersion of the additive through an air nozzle and drying. While the drawing shows the particles to cover substantially all of inside wall surface 19, only a fraction of wall surface 19 need be covered in accordance with the invention.

Stopper 14 may include an annular upper portion 30 which extends over the top edge of side wall 18 and a lower annular portion or skirt 32 which extends into and forms an interference fit with inside wall surface 19 for maintaining stopper 14 in place in open end 20. The invention is not limited to the stopper design shown in the drawing.

The tube may be of any size up to about 50 mm in diameter. A preferred tube is a microcollection tube for small blood samples as from a finger prick. While not wishing to be limited thereby, these tubes are conventionally 43.18 mm long and 6.17 mm internal diameter. The invention is also particularly well suited to evacuated blood collection tubes. Evacuated tubes are generally cylindrical, 50 to 150 mm, preferably 75–130 mm long and about 10–20, preferably 13–16 mm in diameter.

The tube of the invention may be glass or preferably plastic. Suitable plastics are, for example, PET, polypropylene and polystyrene. Likewise, the stopper may be of any elastomer, as is well known in the art of blood collection tubes.

Any conventional gel as known in the art for separating serum or plasma from a cellular fraction may be used. A preferred gel is a thixotropic polyester gel.

The additive may be an anticoagulant or a coagulation enhancer. While heparin, particularly lithium heparin, is the preferred anticoagulant, other conventional anticoagulants, such as sodium citrate or ethylenediaminetetraacetic acid may be used. Suitable enhancers are particulate dispersions of silica, kaolin and the like and enzyme enhancers such as ellagic acid, fibrinogen and thrombin.

Any quantity of additive may be used, generally determined by the area to be covered or the draw volume. While not wishing to be limited thereby, about 1 to 50 ul of additive dispersal may be applied. The dispersal may be of any concentration.

A suitable air nozzle design for use in this invention is that disclosed in U.S. Pat. No. 5,732,885 after being modified to fit into a blood collection tube.

Thus, the additive is applied by spraying, through an air nozzle, a mist of a solvent dispersion, preferably aqueous, to the inside wall surface of the tube. The mist remains on the surface as discrete droplets until dried to leave a uniform coating of individual solid particles.

EXAMPLE 1

Coating of Tube

The inside wall surface of a conventional plastic microcollection tube was misted with an aqueous solution of lithium heparin so that 192 units of heparin were uniformly dispersed over the tube wall. Spraying was performed using an air nozzle dimensioned to fit into the tube. The tubes were dried by blowing hot air through a convection nozzle inserted into the tube. A conventional thixotropic polyester gel was then added to the bottom of the tube and allowed to set. The tube was sterilized with gamma irradiation at 2.5 mrads. The tube was examined visually and the coating was observed to be uniform in distribution and thickness.

EXAMPLE 2

Comparative

Example 1 was repeated exactly except the heparin solution was applied to the tube by spraying from a commercial ultrasonic nozzle. The tube was examined visually and the coating was seen to be non-uniform (localized areas of thick coating and localized areas of light coating) consequent to coalescing and rundown prior to drying.

What is claimed is:

1. A method for coating a blood collection tube comprising spraying a solvent dispersion of an additive to the inside wall surface of a collection tube with an air nozzle and drying said wall surface to leave a coating of additive particles on said wall surface.

2. The method of claim 1 wherein said tube is of polyethylene terephthalate, polypropylene or polystyrene.

3. The method of claim 1 wherein said additive is an anticoagulant or a coagulation enhancer.

4. The method of claim 3 wherein said anticoagulant is heparin, sodium citrate or ethylenediaminetetraacetic acid.

5. The method of claim 3 wherein said coagulation enhancer is a particle of silica or an enzyme.

* * * * *

UNITED STATES PATENT AND TRADEMARK OFFICE

CERTIFICATE OF CORRECTION

PATENT NO. : 6,428,527 B1
DATED : August 6, 2002
INVENTOR(S) : Huw David Jones and Kent Patras It is certified that error appears in the above-identified patent and that said Letters Patent is hereby corrected as shown below:

Title page,
Please substitute the Title page with the attached title page showing the formal drawing.

Drawings,
Please substitute Fig. 1 with the attached Fig. 1 showing the formal drawing.

Signed and Sealed this

Seventeenth Day of December, 2002

JAMES E. ROGAN
*Director of the United States Patent and Trademark Office*

(12) United States Patent
Jones et al.

(10) Patent No.: US 6,428,527 B1
(45) **Date of Patent: *Aug. 6, 2002**

(54) METHOD FOR COATING A BLOOD COLLECTION DEVICE

(75) Inventors: Huw David Jones, Plymouth (GB); Kent Patras, Sargent, NE (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/189,643

(22) Filed: Nov. 10, 1998

(51) Int. Cl.[7] .............................................. A61B 19/00
(52) U.S. Cl. ....................................... 604/403; 427/532
(58) Field of Search ................................ 604/403, 415; 600/476; 428/36.7, 36.91, 446, 448, 500, 702, 413, 480; 220/456, 457; 206/524.2; 427/532

(56) References Cited

U.S. PATENT DOCUMENTS

| | | | | |
|---|---|---|---|---|
| 5,326,535 A | * | 7/1994 | Vogler et al. | 422/102 |
| 5,510,155 A | * | 4/1996 | Williams et al. | 427/532 |
| 5,518,615 A | * | 5/1996 | Vogler et al. | 210/511 |
| 5,686,157 A | * | 11/1997 | Harvey et al. | 428/36.7 |
| 5,732,885 A | | 3/1998 | Huffman | |
| 5,738,920 A | * | 4/1998 | Knors | 428/35.9 |
| 5,763,033 A | * | 6/1998 | Tropsha et al. | 428/36.7 |
| 5,906,744 A | * | 5/1999 | Carroll et al. | 210/516 |
| 5,968,620 A | * | 10/1999 | Harvey et al. | 428/35.9 |
| 6,013,337 A | * | 1/2000 | Knors | 427/579 |

FOREIGN PATENT DOCUMENTS

| | | |
|---|---|---|
| EP | 0 766 973 A1 | 9/1997 |

* cited by examiner

*Primary Examiner*—Dennis Ruhl
(74) *Attorney, Agent, or Firm*—Richard E. Brown

(57) ABSTRACT

A blood collection assembly includes a tube having an open end with a puncturable stopper therein. A thixotropic gel for separating blood components is in the tube and a layer of additive particles is spray dried from an air nozzle onto the inside tube wall. The invention includes a method to make the tube.

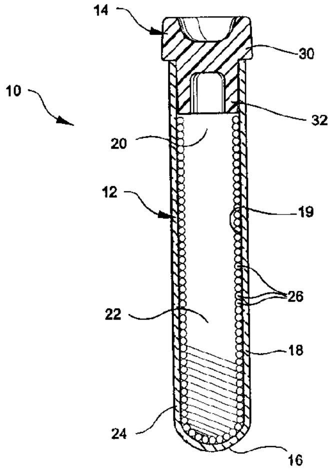

5 Claims, 1 Drawing Sheet